(12) United States Patent
Berberich et al.

(10) Patent No.: US 6,962,590 B2
(45) Date of Patent: Nov. 8, 2005

(54) MEDICAL INSTRUMENT, IN PARTICULAR A RESECTOSCOPE

(75) Inventors: Sascha Berberich, Tuttlingen (DE); Frank Doll, Dürbheim (DE)

(73) Assignee: Karl Storz GmbH & Co. KG, (DE)

( * ) Notice: Subject to any disclaimer, the term of this patent is extended or adjusted under 35 U.S.C. 154(b) by 69 days.

(21) Appl. No.: 10/349,231

(22) Filed: Jan. 22, 2003

(65) Prior Publication Data

US 2003/0144663 A1 Jul. 31, 2003

Related U.S. Application Data

(63) Continuation of application No. PCT/EP01/07580, filed on Jul. 3, 2001.

(30) Foreign Application Priority Data

Jul. 22, 2000 (DE) ............................... 100 35 722

(51) Int. Cl.[7] ............................................ A61B 18/18
(52) U.S. Cl. ...................................................... 606/46
(58) Field of Search .......................................... 606/46

(56) References Cited

U.S. PATENT DOCUMENTS

| | | | |
|---|---|---|---|
| 3,903,892 A | 9/1975 | Komiya | 128/303.15 |
| 4,994,062 A * | 2/1991 | Nishigaki et al. | 606/46 |
| 5,817,128 A * | 10/1998 | Storz | 606/205 |
| 6,039,752 A * | 3/2000 | Kimura et al. | 606/205 |
| 6,730,084 B2 * | 5/2004 | Held | 606/46 |

FOREIGN PATENT DOCUMENTS

| | | |
|---|---|---|
| DE | 25 58 570 | 5/1978 |
| DE | 28 35 649 | 3/1979 |
| DE | 39 17 583 A1 | 3/1990 |
| DE | 39 17 583 C2 | 7/1993 |
| DE | G 93 03 240 | 8/1993 |
| DE | 44 28 479 C2 | 7/1997 |

* cited by examiner

Primary Examiner—Roy D. Gibson
Assistant Examiner—Pete Vrettakos
(74) Attorney, Agent, or Firm—St. Onge Steward Johnston & Reens LLC

(57) ABSTRACT

The invention relates to a medical instrument with a handle on which at least one gripping part, in particular a finger ring, is secured by a connecting clamp in a removable manner and is mounted in rotatable fashion on one handle part, and the connecting clamp consists of a shaft configured on one of the components that are to be connected to one another and of a sheath configured on the other component and where the outer diameter of the shaft, forming an undercut in the area of the free end of the shaft, exceeds the core diameter of the shaft and the inner diameter of the sheath correspondingly has an area forming an undercut and serving to receive the free end of the shaft, with a larger inner diameter, and an area extending in the direction of the sheath opening with a lesser inner diameter. In order to provide a removable placement of the gripping part on the handle, which ensures a secure attachment on the handle, the shaft in the area of the free end having the greater outer diameter is provided with an outer thread and an inner thread is configured in the sheath in the area of the smallest inner diameter.

7 Claims, 3 Drawing Sheets

MEDICAL INSTRUMENT, IN PARTICULAR A RESECTOSCOPE

FIELD OF THE INVENTION

This application is a continuation of pending International Patent Application No. PCT/EP01/07580 filed Jul. 3, 2001, which designates the United States and claims priority of pending German Application No. 10035722, filed Jul. 22, 2000.

The invention relates to a medical instrument, in particular a resectoscope, with a handle on which at least one gripping part, in particular a finger ring, is secured by a connecting clamp in a removable manner and is mounted in rotatable fashion on one part of the handle, and the connecting clamp consists of a shaft configured on one of the components that are to be connected to one another and of a sheath configured on the other component for receiving the shaft and where the external diameter of the shaft, forming an undercut in the area of the free end of the shaft, exceeds the core diameter of the shaft and the inner diameter of the sheath correspondingly has an area forming an undercut and serving to receive the free end of the shaft, with a larger inner diameter, and an area extending in the direction of the sheath opening with a lesser inner diameter.

Resectoscopes are used in surgery in order to remove portions of tissue and/or organs while monitored by an endoscope. To actuate the tool mounted retractably in a hollow shaft, the handle of the resectoscope has a rigid as well as a movable handle part. In order to be able to guide the instrument safely and precisely, a gripping part is normally mounted on the proximal part of the handle in the form of a finger ring, and by means of this gripping part the surgeon can precisely guide the handle part and thus the tool as well. The surgeon's freedom of movement in the process is increased because the finger ring is usually mounted on the one handle part in such a way that it can be freely rotated around the longitudinal axis.

Resectoscopes are in common use in which the finger ring is secured removably on one handle part, in order to be able to adjust the finger rings in size and shape to the respective surgeon, without the necessity of keeping a separate resectoscope available. For this purpose the finger ring of this known resectoscope is mounted rotatably around its longitudinal axis on a plate, which in turn can be screwed together with the movable part of the handle. The finger ring is thus exchanged by unscrewing and replacing the plate bearing the finger ring. Despite the considerable practicality of these resectoscopes, these known medical instruments have the disadvantage that the parts for removably securing the ringer ring on the one part of the handle consist of several parts that are difficult to manufacture, making this configuration very complex and expensive.

A medical instrument of this type is, finally, known from DE 39 17 583 C2. In this known medical instrument configured as a resectoscope, the connecting clamp for securing the at least one rotatable gripping part on the handle is configured so that the shaft connected with the gripping part, forming an undercut on its free end, exceeds the core diameter of the shaft and the sheath configured in the handle for receiving this shaft has an area serving to receive the free end of the shaft, with a larger internal diameter. The free end of the shaft that can be reshaped by means of a slit running in the shaft's longitudinal direction is at first pressed together upon insertion into the sheath, before it can expand again in the area of the sheath with the greater diameter. This expansion causes backward motion of the undercut formed on the shaft and thus a clamped locking of the shaft in the sheath.

Although this known connecting clamp allows a rapid and simple means of securing the gripping part on the handle, along with reasonably priced manufacture, still it is equally easy for the gripping part to be removed again from the handle by merely exerting an axial upward force on the gripping part, so that frequent use of the connecting clamp can result in an unintentional wearing of the clamp during surgical use of the medical instrument if the connecting clamp has become soft.

Consequently, the aim of the invention is to develop a medical instrument of the aforementioned type in such a way that the gripping part first of all can be assembled and disassembled easily on the handle and can be manufactured reasonably and simply, and secondly so that it ensures secure mounting on the handle. To this end, the shaft in the area of the free end with the greater outer diameter is provided with an outer thread and an inner thread is formed in the sheath in the area of the smallest inner diameter.

Although the invention's arrangement of a portion of the thread in the connecting clamp makes assembly and disassembly slightly more difficult, unintentional separation of the gripping part from the handle merely from an axial pressure is completely prevented by this configuration, and thus a medical instrument of this design clearly gives a far better performance.

The gripping part can be connected directly with the handle part or else indirectly connected with the handle part by means of a connector piece, so that the connector piece can be configured as a single unit with the handle part or as a separate adapter piece secured on the handle part.

The clamping of the shaft and sheath can be facilitated if the shaft at least in the area of the free end with the greater outer diameter is configured to be radially reshapable. Secure joining of the connecting clamp here can be ensured if the outer diameter of the shaft in the area of the free end exceeds the inner diameter of the sheath in the area of the smallest inner diameter, so that to be connected the shaft must first be pressed together because of its radial reshapability, before it is expanded again in the undercut, ensuring a firm seating.

To allow the shaft to be radially reshapable, the invention proposes that in the shaft, at least in the area of the free end with the greater outer diameter, at least a slit should be configured running in the longitudinal direction of the shaft. This slit makes it possible to compress the shaft by a spring to overcome the bottleneck in the sheath.

The clamping and loosening of the two components can be facilitated while saving material if start-up inclinations are formed both facing in the axial direction of the shaft at both ends of the area with the greater diameter and also facing in the axial direction of the sheath at both ends of the area with the smallest inner diameter.

A final proposal of the invention is that the gripping part and/or the connector piece be constructed of plastic, especially a pressure die-cast synthetic substance. Configuring at least the gripping part as a pressure die-cast synthetic form makes for a cost-effective and easily manufactured solution.

BRIEF DESCRIPTION OF THE DRAWINGS

Additional characteristics and advantages of the invention can be seen from the following description of the related illustration, in which an embodiment of the medical instru- FIG. 1 Schematic lateral view of a passive resectoscope FIG. 2 Partially cut-out lateral view of a gripping part configured as a finger ring before it is connected with a connector piece FIG. 3 View according to FIG. 2, but showing the ringer ring in the position with the connected connector piece FIG. 4 Reduced view of the finger ring according to FIG. 2.

DETAILED DESCRIPTION OF THE DRAWINGS

Figure 1:
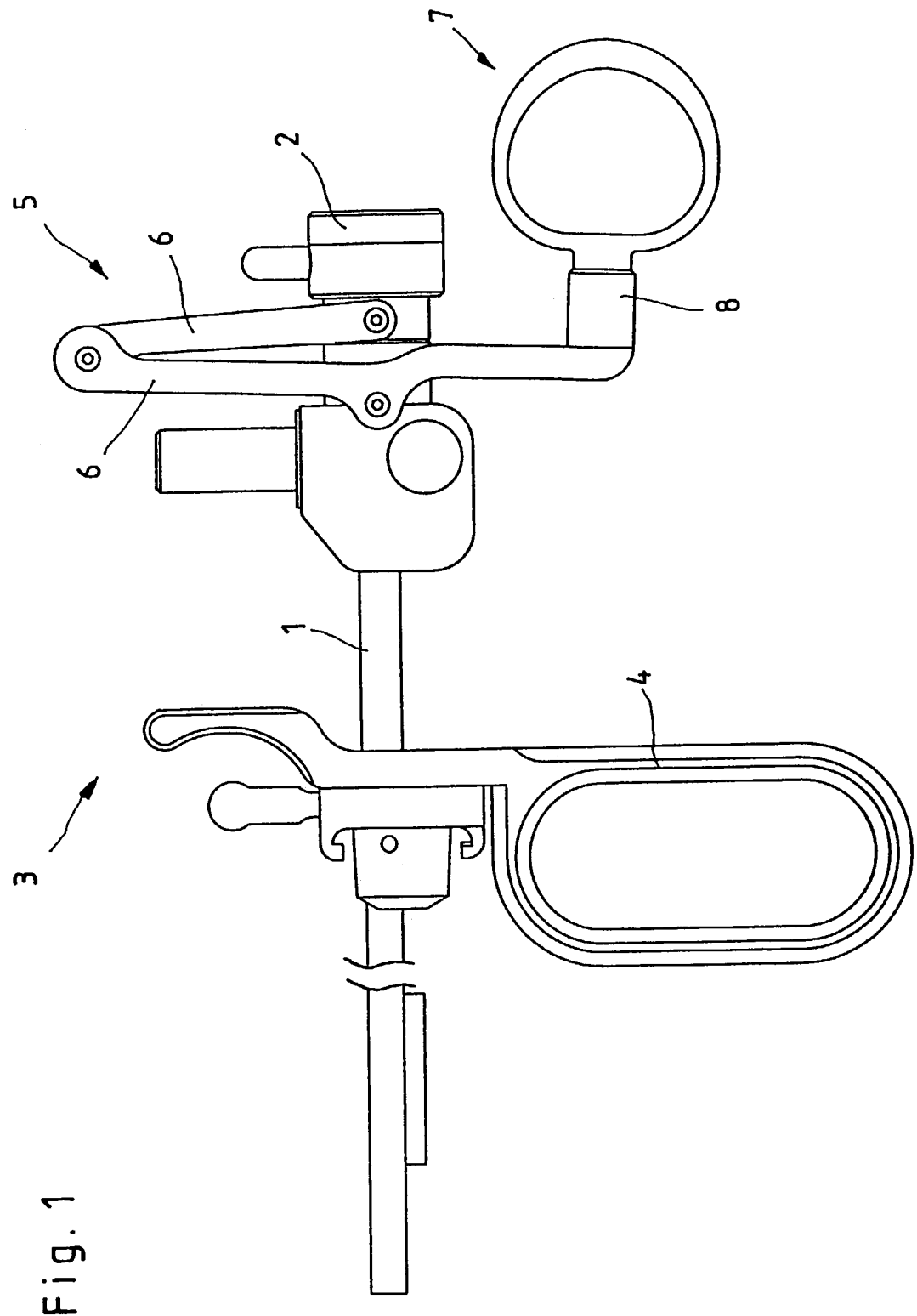

The medical instrument depicted schematically in FIG. 1 is a passive resectoscope. Resectoscopes are used in certain surgical interventions in order to remove portions of tissue under endoscopic observation. The illustrated resectoscope consists essentially of a hollow shaft 1, an endoscope 2 placed in the shaft 1, and a handle 3 mounted at the proximal end of the shaft 1, by means of which a tool, not shown, can be guided parallel to the shaft 1. As can be seen from FIG. 1, the handle 3 consists of a rigid handle part 4 connected to the shaft 1 and a handle part 4 that can be displaced in relation to the rigid handle part 4 to actuate the tool. In the illustrated embodiment the movable handle part 5 is secured on one side to the endoscope 2 by means of a lever mechanism made up of several levers 6 connected flexibly to one another. In passive resectoscopes, this design is exactly reversed. In that case the movable handle part 5 is situated on the distal side. For precise guidance of the movable handle part 5 and thus of the tool, the movable handle part 5 is equipped with a gripping part 7, in particular a finger ring, by means of which the surgeon can guide the tool as desired and sensitively while monitoring it with an endoscope. To ensure the greatest possible freedom of movement for the surgeon, the gripping part 7 is secured on a handle part 4, 5 so that it can rotate freely around the longitudinal axis, that is, proximally on the movable handle part 5 in the case of a passive resectoscope and distally on the rigid handle part 4 for an active resectoscope.

To ensure the best possible additional adjustment of the resectoscope to the individual surgeon, the gripping part 7 is connected with the handle part 5, which is movable in the embodiment, so that it can be removed and replaced, so that gripping parts 7 of various sizes and shapes can be connected without the need to replace the resectoscope.

Figure 2:
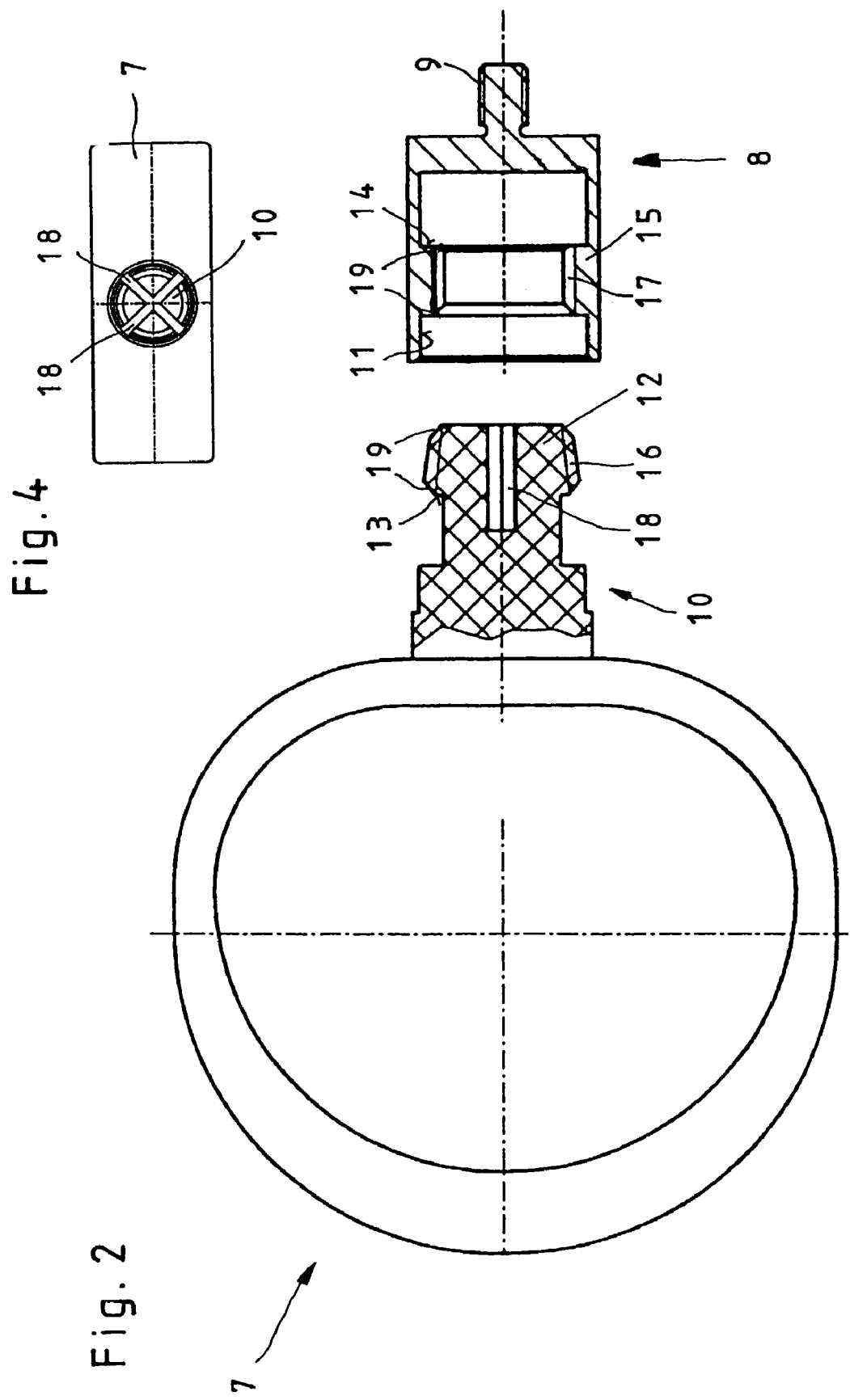
Figure 3:
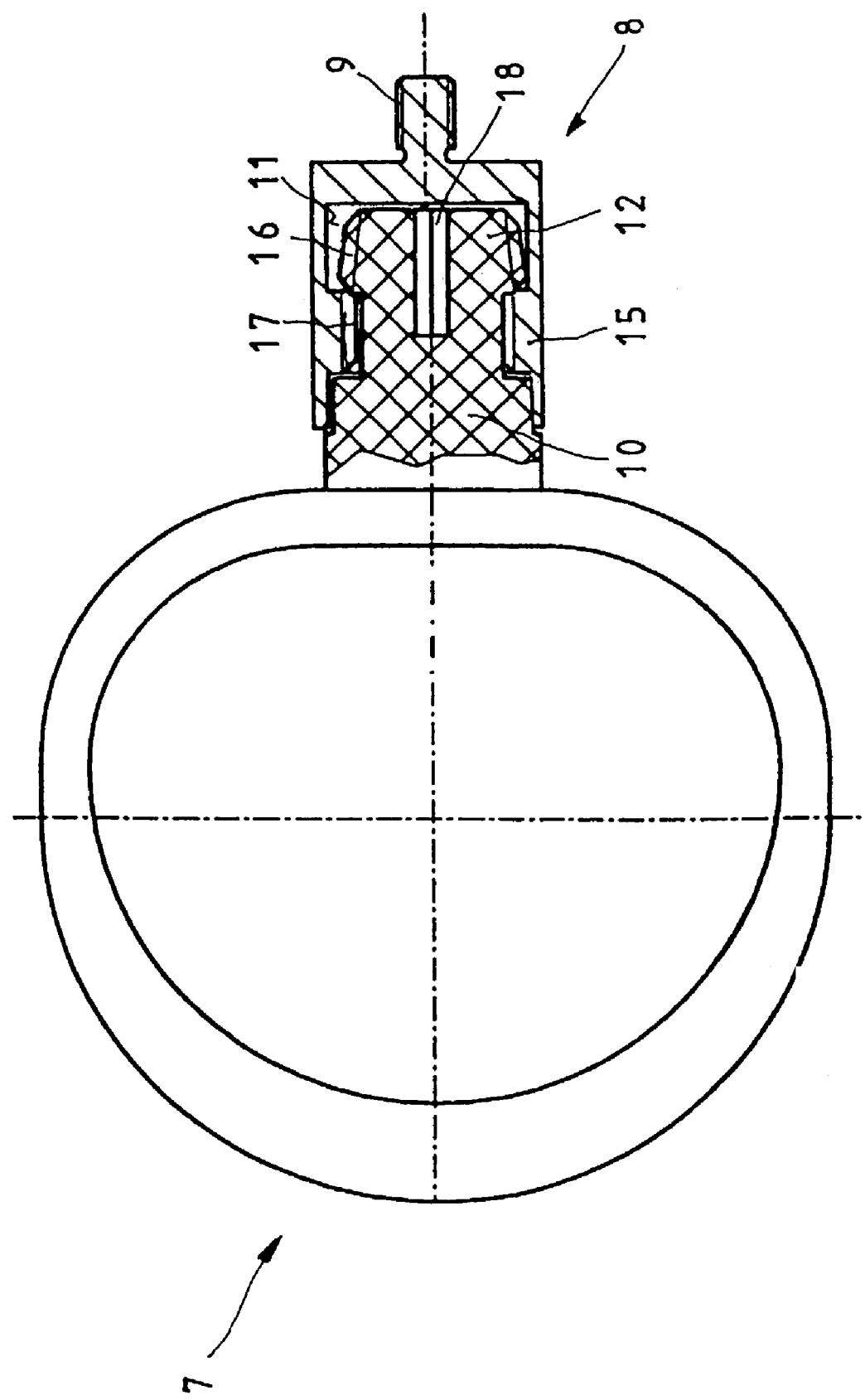

The nature of the connection between the handle part 5 on the one hand and the gripping part 7 on the other can be seen in detail from the illustrations of FIGS. 2 and 3. As shown in the illustrations, the depicted connection is a connecting clamp, with which the gripping part 7 can be secured to a connector piece 8 of the movable gripping part 5. The connector piece 8 here can either form a single unit with the handle part 5 or else can be a separate adapter piece, which in turn can be secured on the handle part 5, for example by a thread 9 on the handle part 5, as shown in FIGS. 2 and 3. It is also possible of course to secure the gripping part 7 directly to a handle part 4, 5 by means of the connecting clamp.

The actual connecting clamp-consists of a shaft 10 configured on one of the components 7 or 8 that are to be connected to one another and a sheath 11 configured on the respective other component 8 or 7 to receive the shaft 10. In the illustrated embodiment, the shaft 10 is configured on the gripping part 7 and the sheath 11 in the connector piece 8.

As can be seen from FIG. 2, the shaft 10 configured on the handle part 7 has areas of diverse outer diameter. To configure the connecting clamp, the outer diameter of the shaft 10 in the area 12 of the free end extends beyond the core diameter in the middle area of the shaft 10, and thus here an undercut 13 is formed by the shift to a greater caliber. The sheath 11 formed in the connector piece 8 and serving to receive the shaft 10 has an inner shape corresponding to the outer contour of the shaft 10 with an area forming an undercut 14 with greater inner diameter, which area serves to receive the area 12 having the larger outer diameter on the free end of the shaft 10. In the direction facing the sheath opening, there begins on the undercut 14 an area 15 with a smaller inner diameter, which is situated in the clamped position in the area of the undercut 13 of the shaft 10, as shown in FIG. 3.

In the illustrated embodiment, the shaft 10 in the area 12 with the greater outer diameter is equipped with an outer thread 16, which preferably is conical in shape and corresponds with an inner thread 17, which is configured in the sheath 11 in the area 15 with the smallest inner diameter.

To provide a secure connecting clamp, which can also resist axially directed blows; the shaft 10 in the area 12 of the greatest outer diameter is configured with small excess with respect to the area 15 of the sheath 11 with the smallest inner diameter. To ensure, despite the excess of the shaft 10, that the connecting clamp can be closed and then opened again, the shaft 10 at least in the area 12 of the greatest outer diameter is configured to be compressible in the radial direction. For this purpose, in the illustrated shaft 10, two slits 18 are formed, crossing one another at perpendicular angle, as can be seen in particular from FIG. 4.

Connecting and disconnecting a gripping part 7 to or from the connector piece 8 of a handle part 4, 5 of the handle 3 occurs as follows:

On the basis of the starting position shown in FIG. 2, in which the connector piece 8 is formed as a separate adapter piece, it is at first necessarily to connect the connector piece 8 with a handle part 4, 5 of the handle 3. In the illustrated case it is the movable handle part 5. For this purpose the connector piece 8 is screwed into a corresponding inner thread of the movable handle part 5 by means of the thread 9.

Then the shaft 10 shaped to the gripping part 7 is inserted into the sheath 11 of the connector piece 8 until the area 12 with the greatest outer diameter on the free end of the shaft 10 reaches the area 15 of the sheath 11 with the smallest inner diameter. By applying an axial pressure, the shaft 10 deformed radially by means of the slit 18 is pushed together to such an extent that the opening of the outer thread 16 formed on the shaft 10 can engage in the inner thread 17 formed in the sheath 11.

Inserting the outer thread 16 into the inner thread 17 is facilitated because the areas 12 and 15 with the greatest outer diameter of the shaft 10 and the smallest inner diameter of the sheath 11 are each equipped on both sides with run-up inclinations 19.

Screwing the shaft 10 into the sheath 11 is continued until the area 12 of the shaft 10 equipped with the outer thread 16 has completely passed the area 15 equipped with the inner thread 17 of the sheath 11 and the area 12 of the shaft 10 with the, greatest outer diameter has entered the area of the sheath 11, in which the undercut 14 is formed. This position, depicting the clamped position, can be seen from FIG. 3.

As soon as the free end of the shaft 10 enters the area of the undercut 14, the radially deformed shaft 10 is again loosened so that the shaft 10 is henceforth held securely in the connecting clamp by means of its larger size in the area of the free end. In this position the shaft 10 is situated in the sheath 11 so that it can freely rotate, so that the area 12 with the greatest outer diameter of the shaft 10 only adjoins the bevel formed in the area 15 of the sheath 11, so that when the shaft 10 or the gripping part 7 is rotated, scarcely any frictional force occurs that can cause material abrasion.

The gripping part 7 is dismantled in the reverse sequence. By applying an axial pulling motion, the shaft 10 is deformed radially to such an extent that the outer thread 16 can engage in the inner thread 17. Then both components, the gripping part 7 and the connector piece 8, are unscrewed from one another until they assume once again the position depicted in FIG. 2.

What chiefly distinguishes this connection clamp between the gripping part on the one hand and the handle 3 on the other is that the components are technically simple as well as economical to produce, for instance as pressure die-cut synthetic parts, and the connector clamp allows the gripping part 7 to be secured in the axial direction while it is simultaneously rotated around the longitudinal axis.

KEY TO REFERENCE NUMBERS

1 shaft
2 endoscope
3 handle
4 rigid handle part
5 movable handle part
6 lever
7 gripping part
8 connector piece
9 thread
10 shaft
11 sheath
12 area of the greatest diameter
13 undercut
14 undercut
15 area of the smallest diameter
16 outer thread
17 inner thread
18 slit
19 start-up inclinations

What is claimed is:

1. Medical instrument, in particular a resectoscope, with a handle on which at least one gripping part, in particular a finger ring, is secured by a connecting clamp in a removable manner and is mounted in rotatable fashion on one handle part of the handle, and the connecting clamp consists of a shaft and a sheath for receiving the shaft, the shaft and sheath configured to be connected to one another, wherein the shaft includes a free end having an outer diameter greater than, a core diameter of the shaft and forming an undercut in the shaft and the sheath includes a sheath opening with a larger inner diameter for receiving the free end of the shaft and a lesser inner diameter, forming an abutment between the larger inner diameter and leser inner diameter corresponding to the undercut of the shaft and serving to receive the free end of the shaft, wherein the shaft in the area of the free end having the greater outer diameter is provided with an outer thread and an inner thread is formed in the sheath in the area of the lesser inner diameter for connection of the shaft with the sheath.

2. Medical instrument according to claim 1, characterized in that the gripping part can be secured on one handle part by means of a connector piece.

3. Medical instrument according to claim 1, characterized in that the shaft is configured to be radially deformable, at least in the area of the free end which has the greater outer diameter.

4. Medical instrument according to claim 1, characterized in that the outer diameter of the shaft in the area of the free end exceeds the inner diameter of the sheath in the area of the lesser inner diameter.

5. Medical instrument according to claim 4, characterized in that in the shaft, at least in the area of the free end having the greater outer diameter, at least one slit is configured extending in the longitudinal direction of the shaft.

6. Medical instrument according to claim 1, characterized in that run-up inclinations are formed, both looking in the axial direction of the shaft at both ends of the area with the greater outer diameter and also looking in the axial direction of the sheath at both ends of the area with the lesser inner diameter.

7. Medical instrument according to claim 1, characterized in that the gripping part and/or the connector piece is made of synthetic material, especially a pressure die-cut synthetic.

* * * * *